United States Patent [19]

Chabardes et al.

[11] 3,944,623
[45] Mar. 16, 1976

[54] ISOMERING OXIDATION OF ETHYLENIC ALCOHOLS TO GIVE ETHYLENIC CARBONYL COMPOUNDS

[75] Inventors: Pierre Chabardes, Lyon; Charles Grard, Chaponost; Charles Schneider, Vernaison, all of France

[73] Assignee: Rhone-Poulenc S. A., Paris, France

[22] Filed: Dec. 18, 1970

[21] Appl. No.: 99,520

[30] Foreign Application Priority Data
Dec. 23, 1969 France .............................. 69.44648

[52] U.S. Cl. ........ 260/603 HF; 260/597 B; 260/598; 260/599; 260/600 R; 260/601 R; 260/602
[51] Int. Cl.² .......................................... C07C 45/16
[58] Field of Search .............................. 260/603 HF

[56] References Cited
UNITED STATES PATENTS

| | | | |
|---|---|---|---|
| 2,011,317 | 8/1935 | Groll | 260/601 R |
| 2,097,154 | 10/1937 | Groll et al. | 260/601 R |
| 2,347,636 | 4/1944 | Spence et al. | 260/603 HF |
| 2,524,865 | 10/1950 | Winslow | 260/603 HF |

FOREIGN PATENTS OR APPLICATIONS

| | | | |
|---|---|---|---|
| 1,019,787 | 2/1966 | United Kingdom | 260/632 R |
| 1,554,805 | 12/1968 | France | 260/601 R |
| 788,921 | 8/1935 | France | 260/601 R |

Primary Examiner—James O. Thomas, Jr.
Assistant Examiner—R. H. Liles
Attorney, Agent, or Firm—Cushman, Darby & Cushman

[57] ABSTRACT

Ethylenic carbonyl compounds are obtained by heating an α-ethylenic tertiary alcohol with oxygen and 0.0001 to 5% by weight, based on the alcohol, of a catalyst comprising a compound of a transition metal of Groups V, VI or VII of the Periodic Table.

15 Claims, No Drawings

ISOMERING OXIDATION OF ETHYLENIC ALCOHOLS TO GIVE ETHYLENIC CARBONYL COMPOUNDS

The present invention relates to a catalytic process for preparing ethylenic carbonyl compounds from tertiary ethylenic alcohols.

The process of the present invention is one wherein an α-ethylenic tertiary alcohol is heated, in the liquid phase, in the presence of oxygen and a catalyst based on a transition metal of sub-Groups V, VI or VII of the Periodic Table in an amount between 0.0001% and 5% by weight of metal relative to the alcohol.

These transition metals are also set out in columns 5b, 6b 7b of the Mendeleev Periodic Classification published in the Handbook of Chemistry and Physics, 45th edition, page B-2.

The α-ethylenic tertiary alcohols used in the process may have the formula:

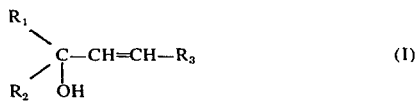

(I)

in which:
R$_1$ and R$_2$ can either
a. be identical or different and each represent a saturated or unsaturated aliphatic or cycloaliphatic radical, or an aromatic or arylaliphatic radical, which radical can optionally contain substituents such as halogen atoms, or hydroxyl, alkoxy, acyl or acyloxy radicals, or can be interrupted by hetero atoms such as O, N, S or functional groups such as —CO— or —CO—NH—, or
b. can together constitute a single divalent alkylene radical —R—, which is saturated or unsaturated, and can optionally contain substituents such as alkyl, cycloalkyl, aryl, aralkyl, hydroxyl, alkoxy, acyl and acyloxy radicals, and halogen atoms, or be interrupted by hetero atoms such as O, N or S, or by functional groups such as —CO— or —CO—NH—, or cycloalkylene or arylene radicals, and R$_3$ represents hydrogen or is as defined above for R$_1$ and R$_2$ under (a).

One particularly valuable class of alcohol which can be used are those having formula (I), in which R$_3$ represents a hydrogen atom.

R$_1$, R$_2$ and R$_3$ preferably contain a total of 2 to 30 carbon atoms, and preferably at least one of the radicals R$_1$ and R$_2$ is an alkyl alkenyl or alkynyl radical having up to 15 carbon atoms and which may optionally be substituted as indicated above.

The ethylenic carbonyl compound obtained by oxidising an alcohol of formula (I) can be represented by the formula

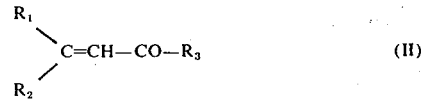

(II)

when R$_1$ and R$_2$ are monovalent radicals. In the case where R$_1$ and R$_2$ together constitute a divalent radical such as the pentamethylene radical, which may optionally be substituted, a β-ethylenic carbonyl compound having a double bond within the ring can also be formed.

The oxygen used in the process of the invention is customarily molecular oxygen; it can be used in the form of pure oxygen or air, or gaseous mixtures containing oxygen; systems capable of liberating oxygen in situ can also be used.

The introduction of molecular oxygen into the medium is generally effected by bubbling the gas in. The gas can be injected in a finely divided form, for the purpose of obtaining a good distribution of the oxygen in the reaction medium; the process can also be carried out while stirring.

The oxidation according to the invention can be effected in the presence of, or in the absence of, a solvent. Compounds which are chemically inert with respect to the catalyst and the reactants are generally used as solvent. Chlorinated or non-chlorinated, aliphatic, alicyclic or aromatic hydrocarbons, ethers and amides are particularly suitable.

In the case where a sufficiently volatile ethylenic alcohol is oxidised in the presence of a solvent, this alcohol can be introduced in gaseous form into a liquid reaction medium heated to the temperature chosen for carrying out the reaction, the said liquid medium principally and initially comprising the solvent and the catalyst. For the purpose of maintaining the temperature constant, a distillation can then be carried out at the rate at which the reaction products are formed.

The reaction temperature is generally between 50° and 250°C, preferably between 100° and 200°C. The pressure can be below, equal to, or above the atmospheric pressure. For economic reasons, pressures below 100 bars are advantageously used.

The catalysts which may be used in the process of the invention are essentially inorganic or organic derivatives of transition metals of sub-Groups V to VII of the Periodic Table; for the purpose of obtaining better yields, derivatives of vanadium, niobium, molybdenum, tungsten or rhenium are preferably used.

Suitable derivatives include the transition metal: halides, chalcogenides, chalcohalides, nitroso-chlorides and nitrosylhalides; salts of oxygen-containing inorganic acids such as sulphates, nitrates, phosphates, carbonates, arsenites, arsenates, germanates, perchlorates, sulphites and nitrites; mixed salts of transition metals of the sub-Groups V to VII with other metals of the Periodic Classification; and salts of aliphatic, cycloaliphatic or aromatic organic acids, such as acetates, propionates, stearates, benzoates, oxalates, succinates, sulphonates, tartrates, citrates, salicylates, naphthenates; or alcoholates or phenates derived from transition metals of sub-Groups V to VII. These salts, alcoholates and phenates can also be salts of oxygen-containing metal radicals, such as vanadyl and molybdenyl salts.

Further suitable inorganic or organic metal derivatives which may be used include salts and esters of acids derived from one or more of these metals, such as vanadates, niobates, tantalates, molybdates, tungstates, and rhenates; the analogous compounds in the per, poly, ortho, meta, pyro, thio or halo form; mixed salts and esters such as tungstovanadates, phosphomolybdates, tartratoniobates, zirconitungstates, molybdocitrates, molybdoformates, molybdolactate, molybdomaleates, molybdomandelates, molybdomucates, molybdooxalates, molybdoquinate, molybdosaccharates, molybdotaetrates, and molybdotungstates; chelates, such as acetylacetonates, which are optionally substituted, for example by aliphatic or cycloaliphatic groups, or by halogen atoms; benzoylacetonates; glyoximates; quinolinates, salicylaldehydates; benzylhydroxamates; derivatives of ethylenediamine, α,α'-bipryridyl, o-nitrosophenol, β-nitrosonaphthol, salicylaldimidine, and of porphyrins; complexes of metals or salts of metals and coordinating substances, such as carbon monoxide, monoolefines, diolefines, polyolefines, acetylenes, cyclopentadienyl, ammonia, cyanides, tertiary nitrogen bases, phosphines, arsines, stibines and nitriles; and organometallic compounds such as alkyl metals.

Catalysts which are particularly well suited for carrying out the invention are products which include a linkage having one of the following formulae:

in which M represents the metal atom, which, in addition, can be joined to other atoms by one or more ionic or covalent bonds. Metal oxides, salts and esters of oxyacids derived from metals, and oxygen-containing salts of metal ions, and salts of chelates such as those derived from β-diketones, belong to this class of catalysts.

The active metal derivative constituting the catalyst can be deposited on a support for example, activated aluminas and silicas, pumice, Fuller's earth, diatomaceous earth, or active charcoal.

The amount of metal contained in the catalyst, relative to the initial weight of the alcohol, is between 0.0001% and 5%, and is preferably between 0.05 and 2%.

The catalyst can be soluble or insoluble in the reaction medium.

Small amounts of a co-catalyst or activator can be used in conjunction with the catalyst. Alcohols, Lewis bases such as ammonia, amines, phosphines, arsines, stibines and bismuthines, and compounds capable of liberating a Lewis base under the reaction conditions, such as, ammonium salts, may be used for this purpose. An excess of co-catalyst is sometimes detrimental to obtaining good yields. The optimum amount of co-catalyst varies, depending on the nature of this co-catalyst and the catalyst.

In the case where the catalyst employed is an ester of an oxyacid derived from a metal of sub-Groups V to VII, it is often advantageous to operate in an anhydrous atmosphere so as to avoid hydrolysis of the catalyst.

The process of the invention can be carried out continuously or discontinuously. At the end of the reaction, the catalyst and the unreacted tertiary alcohol can generally be recovered and used again.

The carbonyl compound obtained at the end of the reaction can be isolated by known methods, for example by distillation or by means of a sulphite or bisulphite addition compound in the case of aldehydes. For certain uses, it is not necessary to isolate the ethylenic carbonyl compound, and the whole of the products constituting the reaction medium can be employed directly. This is particularly the case for the preparation of ionones starting from citral.

The following Examples, illustrate the invention unless otherwise stated, the yields indicated are yields of carbonyl compound obtained, calculated relative to the tertiary alcohol converted in the course of the reaction, and the degree of conversion is equal to the ratio of the amount of tertiary alcohol which has disappeared during the reaction, to the amount of tertiary alcohol employed initially.

EXAMPLES 1 to 5

20 g of linalol and a vanadium catalyst are introduced into a 50 cm³ volume flask provided with a stirrer, a distillation column and a dip tube. Air at the rate of 5 litres/hour is injected into the reaction medium. The nature and the amount of catalyst, the duration and the temperature of heating, and the results obtained are set out in Table 1.

EXAMPLE 6

Example 1 is repeated, using 2.223 g of catalyst in place of 1.484 g, and replacing air by pure oxygen.

Citral is obtained with a degree of conversion of 38.3%, and in a yield of 19.5%.

EXAMPLE 7

Example 1 is repeated, replacing the linalol by nerolidol (3,7,11-trimethyldodecatrien-1,6,10-ol-3).

Farnesal (3,7,11-trimethyldodecatrien-2,6,10-al-1) is obtained with a degree of conversion of 68.1%, and in a yield of 16.3%.

EXAMPLE 8

Example 1 is repeated, 0.205 g of triethanolamine being added.

Citral is obtained with a degree of conversion of 31%, and in a yield of 23.8%.

TABLE 1

| Example | Catalyst Nature | Amount in g | duration of heating | temperature in °C | degree of conversion in% | yield of citral in % |
|---|---|---|---|---|---|---|
| 1 | Tetrahydrolinalyl orthovanadate | 1.484 | 3 hours | 140 | 33.5 | 27 |
| 2 | Ammonium metavanadate | 0.317 | 4 hours, then 1 hour 30 minutes | 130 140 | 31.5 | 22.8 |
| 3 | Vanadyl acetylacetonate | 0.75 | 6 hours 30 minutes | 130 | 42.2 | 21.8 |
| 4 | Triethanolamine orthovanadate | 0.605 | 2 hours, then 3 hours | 130 140 | 39.5 | 14.4 |
| 5 | Cyclohexyl orthovanadate | 1 | 3 hours | 130 | 46.3 | 18.5 |

We claim:

1. A process for the preparation of ethylenic carbonyl compounds of the formulae:

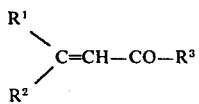

and the tautomers thereof, comprising heating in the liquid phase an ethylenic tertiary alcohol of the formulae:

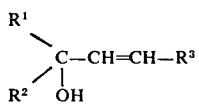

in the presence of oxygen and a catalyst of a compound of the transition metal vanadium, and wherein $R^1$, $R^2$ and $R^3$ are inert under the conditions of the process and $R^1$ and $R^2$ are selected from the group consisting of aliphatic, cycloaliphatic, arylaliphatic and aromatic radicals, and wherein $R^1$ and $R^2$ may represent a divalent radical of 2 to 30 carbon atoms which may be saturated or unsaturated, and wherein the aliphatic, cycloaliphatic, arylaliphatic or aromatic radicals may be substituted by halogen, hydroxy, alkoxy, acyl or acyloxy substituents and $R^3$ may be the same as $R^1$ and $R^2$ or hydrogen.

2. Process according to claim 1 wherein the alcohol is one in which $R_3$ represents hydrogen and $R_1$ and $R_2$ each represent an alkyl, alkenyl or alkynyl radical having upto 15 carbon atoms.

3. Process according to claim 1, wherein the process is carried out at a temperature of 100°–200°C.

4. Process according to claim 1, wherein the process pressure is below 100 bars.

5. Process according to claim 1, wherein the catalyst is present in an amount of 0.05 to 2.0% by weight based on the weight of the alcohol.

6. Process according to claim 1 wherein the catalyst is tetrahydrolinalyl orthovanadate, ammonium metavanadate, vanadyl triethanolamine triethanolamine orthovanadate or cyclohexyl orthovanadate.

7. Process according to claim 1, wherein the starting alcohol is linalol, and the product is citral.

8. Process according to claim 1, wherein the starting alcohol is nerolidol, and the product is farnesal.

9. Process according to claim 1, wherein the catalyst is present in an amount of 0.0001% to 5% by weight based on the weight of the alcohol.

10. Process according to claim 1, wherein the process is carried out at a temperature of 50°–250°C.

11. Process according to claim 1, wherein the catalyst is an ester of an oxyacid derived from said metal.

12. Process according to claim 1, wherein the catalyst is a vanadate.

13. Process according to claim 1, wherein the process is carried out in the presence of a solvent and/or a co-catalyst.

14. Process according to claim 1, wherein the source of oxygen is pure oxygen and/or air.

15. Process according to claim 1, wherein the compound of the transition metal is selected from the group consisting of the halides, chalcogenides, chelates, coordination complexes, alcoholates, oxygen-containing inorganic acid salts of said metals, aliphatic, cycloaliphatic and aromatic organic acid salts of said metals, and the salts and esters of acids derived from said metals.

* * * * *